(12) United States Patent
Dhuper et al.

(10) Patent No.: US 8,534,280 B2
(45) Date of Patent: Sep. 17, 2013

(54) PATIENT INTERFACE MEMBER FOR USE IN AN AEROSOL INHALATION SYSTEM

(75) Inventors: Sunil Kumar Dhuper, Old Westbury, NY (US); Herbert Fred D'Alo, Madison, CT (US)

(73) Assignee: Aeon Research and Technolgy Inc., Hewlett, NY (US)

( * ) Notice: Subject to any disclaimer, the term of this patent is extended or adjusted under 35 U.S.C. 154(b) by 1269 days.

(21) Appl. No.: 11/942,494

(22) Filed: Nov. 19, 2007

(65) Prior Publication Data

US 2009/0126723 A1 May 21, 2009

(51) Int. Cl.
*A61M 16/10* (2006.01)
*A61M 15/00* (2006.01)
*A61M 11/00* (2006.01)
*A62B 9/02* (2006.01)

(52) U.S. Cl.
USPC ............ 128/203.15; 128/200.24; 128/203.12; 128/205.24; 128/200.14; 128/200.23

(58) Field of Classification Search
USPC ............ 128/200.24, 203.12, 203.15, 203.25, 128/204.18, 205.25, 206.12, 206.21, 205.24; 239/338
See application file for complete search history.

(56) References Cited

U.S. PATENT DOCUMENTS

| | | | |
|---|---|---|---|
| 3,057,347 A | 10/1962 | McGee | |
| 3,666,955 A * | 5/1972 | Suprenant et al. | 424/1.11 |
| 3,903,884 A | 9/1975 | Huston et al. | |
| 4,210,155 A | 7/1980 | Grimes | |
| 4,463,755 A | 8/1984 | Suzuki | |
| 4,470,412 A | 9/1984 | Nowacki et al. | |
| 4,637,528 A | 1/1987 | Wachinski et al. | |
| 4,641,644 A | 2/1987 | Andersson et al. | |
| 4,648,628 A | 3/1987 | Meadows et al. | |
| 4,649,912 A | 3/1987 | Collins | |
| 4,823,784 A | 4/1989 | Bordoni et al. | |
| D308,576 S | 6/1990 | Iversen | |
| 4,951,661 A | 8/1990 | Sladek | |
| 4,953,545 A | 9/1990 | McCarty | |
| 5,012,803 A | 5/1991 | Foley et al. | |
| 5,020,530 A * | 6/1991 | Miller | 128/203.28 |
| 5,039,134 A | 8/1991 | Meadows et al. | |
| 5,119,809 A * | 6/1992 | Gerson | 128/203.11 |
| 5,263,485 A | 11/1993 | Hickey | |
| 5,277,175 A | 1/1994 | Riggs et al. | |
| 5,287,849 A | 2/1994 | Piper et al. | |
| 5,349,946 A | 9/1994 | McComb | |
| 5,385,140 A | 1/1995 | Smith | |
| 5,388,571 A | 2/1995 | Roberts et al. | |
| 5,479,920 A | 1/1996 | Piper et al. | |
| 5,482,031 A | 1/1996 | Lambert | |
| 5,546,930 A | 8/1996 | Wikefeldt | |
| 5,586,551 A * | 12/1996 | Hilliard | 128/203.29 |
| 5,613,489 A | 3/1997 | Miller et al. | |
| 5,617,844 A * | 4/1997 | King | 128/200.18 |

(Continued)

*Primary Examiner* — Annette Dixon
(74) *Attorney, Agent, or Firm* — Leason Ellis LLP

(57) ABSTRACT

A device for use in an aerosol inhalation system for delivering aerosolized medication includes a housing that is operatively connected to a source of aerosolized medication such that the aerosolized medication is delivered to the housing. The device also includes a patient interface member removably connected to the housing and being separate therefrom. The patient interface member is in the form of a face mask for placement about a face of the patient and in communication with a mouth of the patient for delivering the aerosolized medication. The patient interface member incorporates an integral inhalation valve and safety feature for protecting against displacement of the inhaltation valve.

13 Claims, 5 Drawing Sheets

(56) References Cited

U.S. PATENT DOCUMENTS

| | | | | |
|---|---|---|---|---|
| 5,640,951 | A | 6/1997 | Huddart et al. | |
| 5,701,886 | A * | 12/1997 | Ryatt | 128/203.12 |
| 5,727,542 | A * | 3/1998 | King | 128/200.18 |
| 5,738,087 | A | 4/1998 | King | |
| 5,752,502 | A | 5/1998 | King | |
| 5,791,340 | A | 8/1998 | Schleufe et al. | |
| 5,813,423 | A | 9/1998 | Kirchgeorg | |
| 5,848,587 | A * | 12/1998 | King | 128/200.18 |
| 5,865,172 | A | 2/1999 | Butler et al. | |
| 5,988,162 | A * | 11/1999 | Retallick, III | 128/203.12 |
| 6,039,042 | A | 3/2000 | Sladek | |
| 6,041,777 | A | 3/2000 | Faithfull et al. | |
| 6,078,730 | A | 6/2000 | Huddart et al. | |
| 6,116,233 | A | 9/2000 | Denyer et al. | |
| 6,192,884 | B1 | 2/2001 | Vann et al. | |
| 6,340,023 | B2 | 1/2002 | Elkins | |
| 6,363,932 | B1 | 4/2002 | Forchione et al. | |
| 6,390,090 | B1 | 5/2002 | Piper | |
| 6,427,685 | B1 | 8/2002 | Ray | |
| 6,450,163 | B1 | 9/2002 | Blacker et al. | |
| 6,494,202 | B2 | 12/2002 | Farmer | |
| 6,550,476 | B1 | 4/2003 | Ryder | |
| 6,612,308 | B2 * | 9/2003 | Stenzler et al. | 128/205.11 |
| 6,622,725 | B1 | 9/2003 | Fisher et al. | |
| 6,679,252 | B2 | 1/2004 | Sladek | |
| 6,748,945 | B2 | 6/2004 | Grychowski et al. | |
| 6,772,754 | B1 | 8/2004 | Mendenhall | |
| 6,776,160 | B2 | 8/2004 | Wang | |
| 6,799,423 | B2 | 10/2004 | Piekarski | |
| 6,929,003 | B2 | 8/2005 | Blacker et al. | |
| 6,976,488 | B2 | 12/2005 | Halperin | |
| 6,994,083 | B2 | 2/2006 | Foley et al. | |
| 7,036,500 | B2 | 5/2006 | Niles et al. | |
| 7,080,643 | B2 | 7/2006 | Grychowski et al. | |
| 7,131,439 | B2 | 11/2006 | Blacker et al. | |
| 7,191,776 | B2 | 3/2007 | Niles et al. | |
| 7,204,245 | B2 | 4/2007 | Johnson et al. | |
| 7,290,541 | B2 | 11/2007 | Ivri et al. | |
| 7,445,006 | B2 * | 11/2008 | Dhuper et al. | 128/203.12 |
| 7,493,898 | B2 | 2/2009 | King | |
| 7,743,764 | B2 * | 6/2010 | Dhuper et al. | 128/200.14 |
| 7,841,342 | B2 * | 11/2010 | Dhuper et al. | 128/203.15 |
| 2002/0017302 | A1 | 2/2002 | Fukunaga et al. | |
| 2002/0121275 | A1 | 9/2002 | Johnson et al. | |
| 2002/0129814 | A1 | 9/2002 | Sladek | |
| 2003/0010336 | A1 | 1/2003 | Vito | |
| 2003/0209246 | A1 | 11/2003 | Schroeder et al. | |
| 2004/0011364 | A1 | 1/2004 | Dhuper et al. | |
| 2004/0024372 | A1 | 2/2004 | Grogan | |
| 2004/0060560 | A1 * | 4/2004 | Stenzler et al. | 128/206.21 |
| 2004/0084048 | A1 * | 5/2004 | Stenzler et al. | 128/206.12 |
| 2004/0123974 | A1 | 7/2004 | Marler et al. | |
| 2004/0226563 | A1 | 11/2004 | Xu et al. | |
| 2004/0234610 | A1 | 11/2004 | Hall et al. | |
| 2005/0028811 | A1 * | 2/2005 | Nelson et al. | 128/200.11 |
| 2005/0092325 | A1 | 5/2005 | Dionne | |
| 2006/0231090 | A1 | 10/2006 | King | |
| 2006/0231091 | A1 | 10/2006 | Camarillo | |
| 2006/0249158 | A1 * | 11/2006 | Dhuper et al. | 128/206.28 |
| 2006/0260607 | A1 * | 11/2006 | Dhuper et al. | 128/200.21 |
| 2007/0062531 | A1 * | 3/2007 | Fisher et al. | 128/204.23 |
| 2007/0068516 | A1 * | 3/2007 | Dhuper et al. | 128/200.23 |
| 2007/0137644 | A1 | 6/2007 | Dhuper et al. | |
| 2008/0087280 | A1 * | 4/2008 | Dhuper et al. | 128/200.23 |
| 2009/0173348 | A1 * | 7/2009 | Fisher et al. | 128/205.12 |

* cited by examiner

PATIENT INTERFACE MEMBER FOR USE IN AN AEROSOL INHALATION SYSTEM

CROSS-REFERENCE TO RELATED APPLICATION

The present application is related to Applicants' other U.S. patent applications Ser. Nos. 11/121,688, filed May 3, 2005, now U.S. Pat. No. 7,445,006, issued Nov. 4, 2008; 11/414,737, filed Apr. 27, 2006, now U.S. Pat. No. 7,841,341, issued Nov. 30, 2010, and 11/623,221, filed Jan. 15, 2007, now U.S. Pat. No. 7,841,342, issued Nov. 30, 2010, each of which is hereby incorporated by reference in its entirety.

TECHNICAL FIELD

The present invention relates to inhalation equipment and more particularly, relates to aerosol inhalation systems including a patient interface member (accessory) for use in the system between a conventional part of the inhalation equipment, such as a generator, and the patient to provide in a number of applications a completely closed system that ensures that the medication delivered to the patient has a fixed concentration over time and is optimized.

BACKGROUND

Aerosol inhalation equipment is commonly used as a means to deliver medication in an aerosolized form to a patient. Aerosolized medication is typically used to treat patients with respiratory conditions, such as asthma or chronic obstructive pulmonary disease (COPD). For example, inhalation equipment is a common means for delivering medication to counter certain aliments of a patient population, including reactive airway disease, asthma, cystic fibrosis, etc.

It is generally accepted that effective administration of medication as aerosol depends on the delivery system and its position in relation to the patient. Aerosol particle deposition is influenced by particle size, ventilatory pattern, and airway architecture and effective medication response is also influenced by the dose of the medication used.

An aerosol delivery system includes three principal elements, namely a generator, a power source, and an interface. Generators include small volume nebulizers (SVN), large volume nebulizers (LVN), metered dose inhalers (MDI), and dry powder inhalers (DPI). The power source is the mechanism by which the generator operates or is actuated and includes compressed gas for SVN and LVN and self-contained propellants for MDI. The interface is the conduit between the generator and the patient and includes spacer devices/accessory devices with mouthpieces or face masks. Depending on the patient's age (ability) and coordination, various interfaces are used in conjunction with SVN and MDI in order to optimize drug delivery.

A SVN is a jet nebulizer that is powered by a compressed gas source. The medication is displaced up a capillary tube from the nebulizer's reservoir and is dispersed continuously as aerosolized particles. The aerosolized particles are spontaneously inhaled by the patient or delivered in conjunction with positive-pressure breaths. Typically, for patients greater than 3 years who are spontaneously breathing without an artificial airway and are able to cooperate, a mouthpiece with an extension reservoir should be used. For patients unable to negotiate a mouthpiece, typically children under 3 years, a face mask should be used.

An MDI is essentially a pressurized canister that contains a medication and propellant. Actuation of the MDI results in the ejection of one dose of medication as aerosolized particles, which can be spontaneously inhaled by the patient or delivered in conjunction with positive-pressure breaths. A spacer device/accessory device should be used with an MDI. A spacer device enhances delivery by decreasing the velocity of the particles and reducing the number of large particles. A spacer device with a one-way valve, i.e., holding chamber, eliminates the need for the patient to coordinate actuation and inhalation and optimizes drug delivery. A spacer device without valves requires coordination between inhalation and actuation. The MDI with spacer device and face mask is appropriate for patients, typically less than 3 years, unable to use a mouthpiece.

A DPI is a breath-actuated device that uses a gelatin capsule containing a single dose of medication and a carrier substance to aid in the dispersion of the drug. The capsule is inserted into the device and punctured. The patient's inspiratory flow disperses the dry particles and draws them into the lower airways. In spontaneously breathing patients, this device is appropriate in patients who are able to achieve a certain inspiratory flow, such as equal to or greater than 50 L/min. This will typically correspond to children about 6 years or greater.

A LVN can be used to deliver a dose of medication continuously over a period of time. A LVN is powered by a compressed gas source, and a face mask is typically used as the interface.

The two primary means for delivering aerosolized medication to treat a medical condition is an MDI or a nebulizer. MDI medication (drug) canisters are typically sold by manufacturers with a boot that includes a nozzle, an actuator, and a mouthpiece. Patients can self-administer the MDI medication using the boot alone but the majority of patients have difficulty in synchronizing the actuation of the MDI canister and patient inhalation and improve the delivery and improve the delivery of medication by decreasing oropharyngeal deposition of the aerosol drug.

Many valved chambers of this type are commercially available. Examples of such spacers include but are not limited to those structures disclosed in U.S. Pat. Nos. 4,470,412; 5,012,803; 5,385,140; 4,637,528; 4,641,644; 4,953,545; and U.S. patent application publication No. 2002/0129814. These devices are expensive and may be suitable for chronic conditions that require frequent use of MDI inhalers provided the cost and labor involved in frequent delivery of medication is acceptable to the patient. However, under acute symptoms, such devices may fail to serve the purpose and lead to an inadequate delivery of medication.

Aerosol delivery systems that use standard small volume nebulizers are commonly used in acute conditions as they are cheap and overcome the inhalation difficulties associated with actuation of MDI and synchronization of inhalation by the patient. Nebulizers are fraught with numerous problems as well. The medication dose used is about 10 times of that used with an MDI and hence the increased cost without any added proven clinical benefit. Secondly, the majority of the nebulized medication is wasted during exhalation. Thirdly, the time taken to deliver the medication is several times that of an MDI and the labor cost of respiratory therapist may outweigh the benefits of nebulizers compared with MDIs. Breath actuated nebulizers(s) with reservoir have been designed to overcome the medication waste. An example of this type of device is found in U.S. Pat. No. 5,752,502. However, these devices are expensive and still have all the other problems associated with nebulizer use alone. Other examples of aerosol inhalation devices can be found in U.S. Pat. No. 4,210, 155, in which there is a fixed volume mist accumulation chamber for use in combination with a nebulizer and a TEE connection.

Problems with prior art devices include that the devices significantly waste medication, they provide a non-uniform concentration of delivered medication, they are expensive, and they are difficult to use. Many of these devices are commercially available in which the nebulizer is directly attached to the TEE connector without any mixing chamber. All of the aforementioned devices can be used with either an MDI or a nebulizer but not both, and hence, face the difficulty associated with either system alone. Other devices have tried to overcome the above problems by incorporating a mixing chamber in the device with adaptability to be used with an MDI or standard nebulizer. U.S. patent application publication No. 2002/0121275 disclosed a device having the above characteristics. However, this device is plagued with problems that are typical to those type of devices. As with other conventional devices, the disclosed device, like the other ones, fails to incorporate some of the key features necessary for enhanced aerosol delivery.

In general, each of the prior art devices suffers from the following deficiencies: (1) the entrained airflow in the device interferes with the MDI plume as well as the plume generated by a nebulizer resulting in increased impaction losses of aerosol generated by either an MDI or nebulizer; (2) the device does not have the ability to deliver a desired precise fraction of inspired oxygen to a hypoxic patient and simultaneously deliver aerosol medication with either a metered dose inhaler (MDI) or a nebulizer; (3) the device can not deliver a gas with a desired density to improve aerosol delivery and a desired fraction of inspired oxygen to a hypoxemic patient; (4) the device does not have the ability to deliver different density gases with a desired fraction of inspired oxygen simultaneously while retaining the ability to deliver aerosol medication at the same time with either an MDI or a nebulizer; (5) the device does not have the ability to deliver a mixture of multiple gases to a patient and simultaneously maintain a desired fraction of inspired oxygen; (6) the device does not serve as a facemask for delivering varying concentrations of inspired oxygen from room air to 100% but serves solely as an aerosol delivery device; (7) the device does not have a reservoir chamber—either as a bag or as a large volume tubing to store nebulized medication that is otherwise wasted during exhalation (The holding chamber of this type of device varies from 90 cc to 140 cc and is not enough to serve as a reservoir for the volume of nebulized medication generated during exhalation is wasted); (8) there is no mechanism in the device to prevent entrainment of room air which forms the bulk of volume during inhalation (the fraction of inspired oxygen and the density of the gas mixture inhaled by the patient may vary with every breath with the device depending on the volume of entrained room air which may vary with each breath); (9) the device does not have any valve system to prevent exhaled carbon dioxide from entering the holding chamber—rebreathing of carbon dioxide from the holding chamber on subsequent inhalation can be extremely detrimental to a patient and extremely dangerous under certain clinical conditions; (10) the device does not have the capability of delivering medication with an MDI and a nebulizer simultaneously; and (11) the device has a fixed volume-holding chamber, which makes the device extremely large and cumbersome to deliver medication.

What is needed in the art and has heretofore not been available is a system that overcomes the above deficiencies and incorporates functionality to make the device a compact, user friendly, economical, and multipurpose aerosol device for both acute and chronic use with either an MDI or a nebulizer or with both devices simultaneously as warranted by the patient's clinical circumstances.

SUMMARY

A device for use in an aerosol inhalation system for delivering aerosolized medication includes a means for generating aerosolized medication and a housing that is operatively connected to the means for generating aerosolized medication such that the aerosolized medication is delivered to the housing. The device also includes a patient interface member removably connected to the housing and being separate therefrom. The patient interface member is for placement about a face of the patient and in communication with a mouth of the patient for delivering the aerosolized medication. The patient interface member incorporates a first flow control means that is positionable between an open position where aerosolized medication flows into an interior of the patient interface member when the patient inhales and a closed position when the patient exhales. The exhaled gas is vented from the interior through at least one vent port that is part of the patient interface member.

According to one embodiment, a method of delivering aerosolized medication to a patient includes the steps of providing a single gas source that has a main gas flow; dividing the main gas flow to a first flow path that is delivered to a nebulizer device for generating the aerosolized medication and a second flow path that is delivered to an accessory that mates with a patient interface member for delivering the aerosolized medication to the patient; creating a primary flow path where the aerosolized medication flows directly to the patient interface member without passing through a flow control means; storing gas that flows along the second flow path within a first reservoir that is fluidly connected to the accessory; creating a secondary flow path for delivering the gas that is stored in the first reservoir to the patient interface member, wherein the gas within the first reservoir flows through a secondary flow control means before entering the patient interface member and therefore, the secondary flow path has a greater flow resistance compared to the primary flow path; and opening a primary flow control means that is part of the patient interface member when the patient inhales to permit gas that flows along the primary flow path to be delivered to the patient, wherein the secondary flow control means opens when the patient inhales to permit gas to flow from the first reservoir to the patient interface member when flow of the gas along the primary flow path is insufficient.

Further aspects and features of the exemplary aerosol inhalation system disclosed herein can be appreciated from the appended Figures and accompanying written description.

BRIEF DESCRIPTION OF THE DRAWING FIGURES

The foregoing and other features of the present invention will be more readily apparent from the following detailed description and drawings of the illustrative embodiments of the invention wherein like reference numbers refer to similar elements and in which.

DETAILED DESCRIPTION OF PREFERRED EMBODIMENTS

Figure 1:
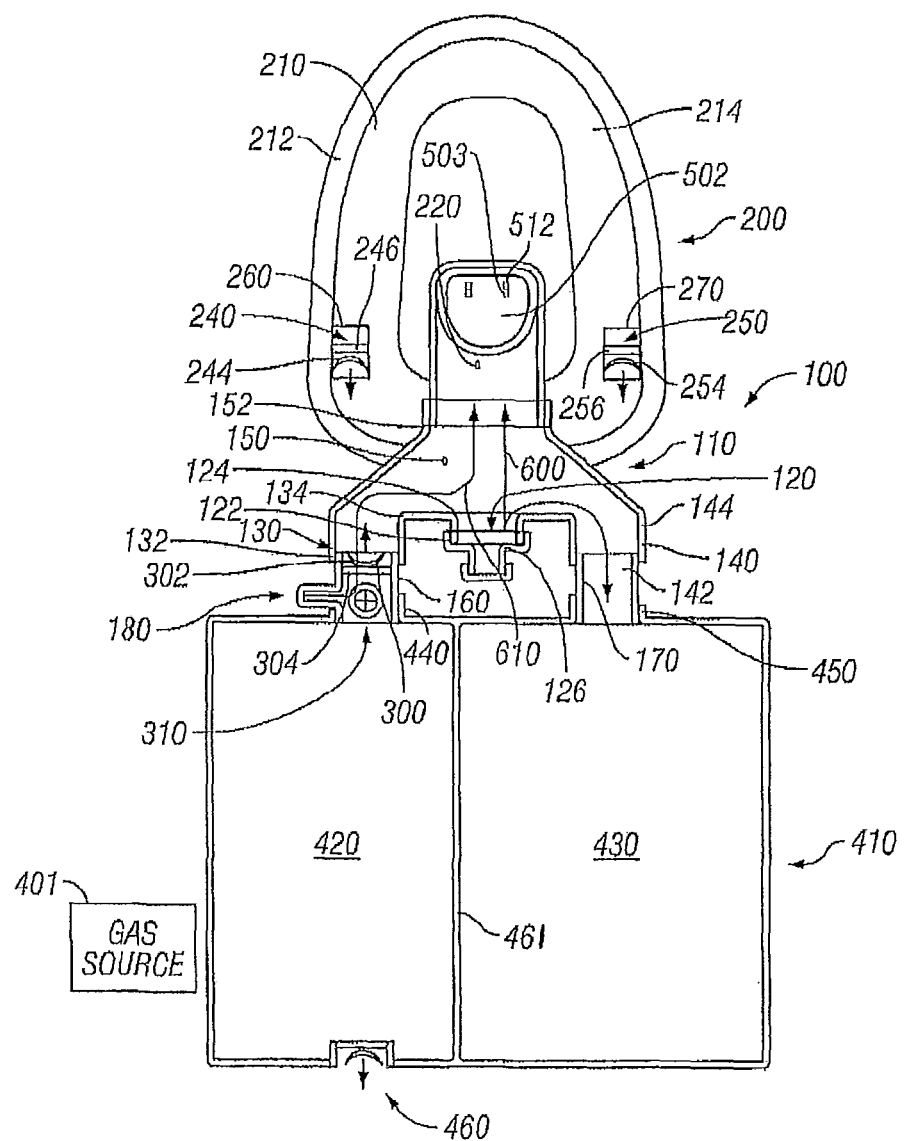
FIG. 1 is a front elevation view of a patient interface member for use in an aerosol inhalation system according to a first embodiment.
Figure 2:
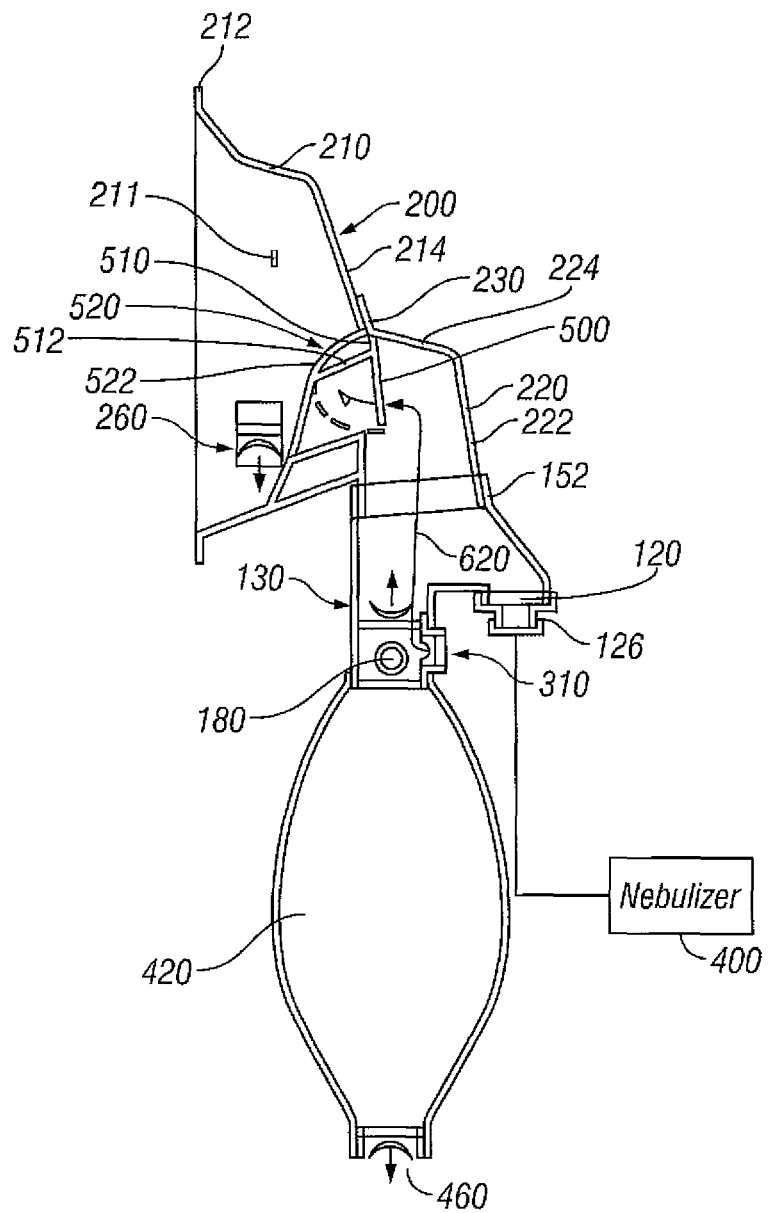
FIG. 2 is a cross-sectional view of the patient interface member of FIG. 1.
Figure 3:
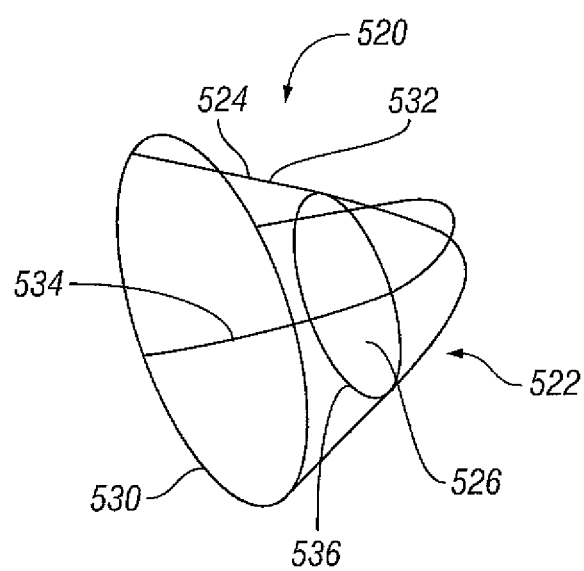
FIG. 3 is a perspective view of one exemplary safety valve feature according to one exemplary embodiment.

Now turning to FIGS. 1-2 in which an accessory or patient interface system 100 according to one exemplary embodiment and for use in an aerosol delivery system is illustrated. As described below, the system 100 is intended particularly for use with a nebulizer; however, it can be adapted for use with other aerosol generating devices, such as an MDI.

Unlike conventional interface accessories that are meant to be attached between the equipment that generates the aerosolized medication and a patient interface (face mask), the system 100 of the present invention is constructed so that the patient interface member (e.g., a face mask) that directly contacts the patient's face is an integral part of the system and in particular, the accessory component that is attached to the source of gas. Accordingly, the system 100 of the present invention needs only be attached to the device that generates the aerosolized medication, e.g., a nebulizer.

The system 100 has a main body 110 that generally has the shape of a legged structure. For example, the main body 110 can be in the form of a tripod structure and therefore, includes a first leg 120, a second leg 130 and a third leg 140. The orientation of the legs 120, 130, 140 is not critical; however, in the illustrated embodiment, the legs 120, 130, 140 are substantially parallel to one another and are oriented in a triangular manner. The first leg 120 has a free distal end 122 and a proximal end 124 that is in communication with a main body section 150. The second leg 130 has a free distal end 132 and a proximal end 134 that is in communication with the main body section 150 and similarly, the third leg 140 has a free distal end 142 and a proximal end 144 that is in communication with the main body section 150. The first, second and third legs 120, 130, 140 can have tubular structures, such as circular shaped tubular structures.

It will also be appreciated that the lengths of the legs 120, 130, 140 and the diameters of the legs 120, 130, 140 can vary and in particular, the lengths and diameters can be the same or one or more of the legs 120, 130, 140 can have a different length and/or diameter. In the illustrated embodiment, the first leg 120 has a slightly smaller length than the other legs 130, 140.

The main body section 150 is in communication with the legs 120, 130, 140 in that the proximal ends 124, 134, 144 form entrances into the main body section 150. The main body section 150 thus defines a main chamber where fluids from the legs 120, 130, 140 can interact and conversely, fluid in the main chamber can be routed to one or more of the legs 120, 130, 140.

The main body section 150 includes a patient interface port 152 that is configured to mate with a patient interface member, such as a mask 200 or a mouthpiece (not shown) or the like. As with the other legs 120, 130, 140, the patient interface port 152 can be in the form of a tubular structure that is configured to mate with the patient interface member 200. As described below in more detail, according to one embodiment, the patient interface port 152 is a tubular structure or leg that is designed to mate with a complementary protruding structure that is part of the mask 200. In the illustrated embodiment, the main body section 150 has a tapered construction, such as an inward taper, that leads to the patient interface port 152.

The main body 110 can be formed of a number of different materials, including plastic.

The first leg 120 is for connection to a source of aerosolized medication that is to be delivered to a patient through the patient interface member 200. For example, the first leg 120 can be connected to a nebulizer, which as is commonly known, is a machine that generates an aerosolized medication. It will also be appreciated that there are other types of devices that generate aerosolized medication. For example, an MDI type device can be configured to mate with and be used with the main body 110.

A cap 126 can be used to plug the tubular structure that forms the first leg 120. The cap 126 can be attached to the body 110 by a tether or the like. The cap 126 thus closes off the first leg 120 and prevents fluid from flowing into or out of the first leg 120 when the nebulizer is not attached.

In the illustrated embodiment, the second and third legs 130, 140 lie in one vertical plane, while the first leg 120 lies in another vertical plane. Preferably, each of the entrances (proximal ends 124, 134, 144) of the legs 120, 130, 140 lies in the same horizontal plane. In a normal operating position, shown in FIG. 1, the patient interface port 152 faces upward, while the legs 120, 130, 140 face downward.

The second leg 130 is designed to receive supplemental gas flow, as described below, while the third leg 140 provides communication between the main body 110 and a fluid storage member as described below.

The main body 110 includes a first fluid connector 160 that is complementary to and mates with the second leg 130 and a second fluid connector 170 that is complementary to and mates with the third leg 140. The connectors 160, 170 can be attached to the legs 130, 140 using any number of conventional techniques, including but not limited, to a frictional fit or any other type of mechanical fit, such as snap-fit or the use of fasteners. In the illustrated embodiment, the connectors 160, 170 are in the form of tubular structures that are received within the legs 130, 140, respectively.

The first fluid connector 160 has a number of functional parts since it is associated with the supplemental gas flow. For example, the first fluid connector 160 has a supplemental gas port 180 that extends outwardly from the tubular connector 160. The supplemental gas port 180 can be in the form of a tubular structure, e.g., nipple or nozzle-like structure. The first fluid connector 160 has a first flow control means 300 that is disposed therein for controlling the flow of the fluid through the fluid connector 160 into the main body section 150 and also, for preventing fluid flow from the main body section 150 into the fluid connector 160. The first flow control means 300 can be in the form of a one way valve and in this case, the first flow control means 300 is an inhalation valve.

In one aspect, the supplemental gas port 180 is a metered port that permits the flow rate of the supplemental gas to be controlled. A detailed description of the function of the metered port is set forth in applicant's pending U.S. patent application Ser. No. 11/623,221, which is hereby incorporated by reference in its entirety. In addition, other flow metering techniques can be used.

The first flow control means 300 includes a valve element 302 which is positionable between an open position and a closed position and can be any number of different type of valve structures so long as they function in the intended manner and provide the desired results. The valve 302 typically seats against a valve seat 304 and when the valve 302 is a one-way flap valve, it presses against the valve seat 304 on exhalation and completely occludes the open end of the fluid connector 160. On inhalation, the flap valve 302 moves away from (e.g., lifts off) the flap valve seat 304 to permit supplemental gas to flow through the second leg 130 into the main body section 150 and to the patient as described below.

In terms of the relative positions of the components and features, the valve 302 is located at a proximal end of the connector 160 and the supplemental gas port 180 is located below the valve 302.

The connector 160 also includes an inhalation safety valve 310 that opens to atmosphere under select conditions. The precise function and operation of the safety valve 310 are described in more detail below. However, in general, if additional fluid flow is needed as when the supplemental gas flow is not providing enough flow or in the event, that the supplemental gas flows becomes obstructed or fails, an emergency fluid flow of atmospheric air is provided to the patient to permit normal inhalation.

The inhalation safety valve 310 is disposed below the first flow control means 300 and can be formed generally in the same horizontal plane as the supplemental gas port 180. When the supplemental gas port 180 and the safety valve 310 are located in the same plane, one is offset by a predetermined angle from the other. For example, the safety valve 310 can be offset 45 degrees from the supplemental gas port 180. Accordingly, when air does flow through the safety valve 310, the air must also pass through the first flow control means 300 and therefore, before the air flows into the main conduit section 150 and to the patient interface member 200, the air must pass through two separate flow control means, e.g., two inhalation valves. In contrast, the supplemental gas flowing through the supplemental gas port 180 must pass only through a single flow control means, namely, the first flow control means 300, in order to enter the main body section 150 and flow to the patient interface member.

In one particularly preferred embodiment, the accessory 100 is intended for use with a nebulizer, generally indicated at 400, and therefore includes a holding chamber 410 into which the aerosol particles can be stored prior to the patient inhaling. The holding chamber 410 is preferably formed as a member that is collapsible and expandable depending upon whether gas is being delivered thereto or being evacuated therefrom. The holding chamber 410 thus can have a number of different structures that have a variable dimension, such as a variable length or a variable width. In one embodiment, the holding chamber 410 is defined by a bellows-type structure that can either expand or collapse/constrict depending upon the force applied. As with other accessories of this type, the holding chamber 410 is intended to receive and store the aerosol particles prior to the patient inhaling them by means of the accessory 100 and the facemask 200.

In the illustrated embodiment, the holding chamber 410 is in the form of an expandable/collapsible bag (reservoir bag). According to one aspect of the present invention, the holding chamber 410 is in the form of a bi-furcated bag or the like as shown in FIG. 1. More specifically, the bag 410 is bi-furcated and has two independent distinct compartments, namely a first compartment 420 and a second compartment 430. Since the two compartments 420, 430 are distinct from one another (no fluid communication therebetween), the bag 410 has a first port 440 that forms an entrance and is in fluid communication with the first compartment 420, as well as a second port 450 that forms an entrance and is in fluid communication the second compartment 430. A separating wall or membrane 461 is formed as part of the bag 410 and serves to divide the bag 410 into the first and second compartments 420, 430. The body of the bag 410, as well as the separating wall 461, is preferable formed of a flexible material, such as a fabric that permits the bag 410 to either expand as when fluid enters the bag 410 or contract (collapse) as when the fluid is evacuated from the bag 410. The first port 440 is formed on one side of the separating wall 461, while the second port 450 is formed on the other side of the separating wall 461.

The first port 440 and the second port 450 can each be in the form of a hollow tubular conduit structures. The ports 440, 450, thus have a complementary structure to the first and second connectors 160, 170, respectively, and in particular, the ports 440, 450 sealingly engage and are coupled to the connectors 160, 170. For example, the connectors 160, 170 can be inserted into and frictionally held within the ports 440, 450 so as to couple the bag 410 to the main body section 150. Other techniques besides a frictional fit, including a snap fit or the like, can also be used.

In one embodiment, one of the first and second compartments 420, 430 is associated with the nebulizer 400 and more particularly, serves as a holding chamber for the nebulized medication that is generated by the nebulizer 400. The other of the compartments 420, 430 is associated with a supplemental gas source and serves as a supplemental gas holding chamber that supplements the nebulized medication when needed as explained in detail below.

In the illustrated embodiment, the first compartment 420 that is associated with the supplemental gas flow has a smaller volume compared to the second compartment 430 that stores the nebulized medication. For example, the first compartment 420 can have a 600 ml volume, while the second compartment 430 can have a 900 ml volume. However, it will be appreciated that the compartments 420, 430 can have different volumes and in one embodiment, the two compartments 420, 430 can have the same volume. In other words, the second compartment 430 that serves as the nebulizer holding compartment can have a greater volume than the first compartment 420 which receives the supplemental gas to backup the nebulized medication holding chamber.

It will also be understood that the connectors 160, 170 can be eliminated and the storage or holding chamber can be directly connected to the respective second and third legs 130, 140. In this case, the first and second ports 440, 450 directly engage and are secured to the second and third legs 130, 140. The first port 440 would include the supplemental gas port 180, the first flow control means 300 and the safety valve 310.

The supplemental gas port 180 and the inhalation safety valve 310 are formed in locations where they do not interfere with the insertion of the connectors 160, 170 into the corresponding first and second ports 440, 450. In particular, when the connector 160 is inserted into the first port 440, the supplemental gas port 180 is located at a position such that a top edge of the first port 440 abuts a bottom edge of the supplemental gas port 180. The safety valve 310 is similarly located at a position where it is not obstructed by the first port 440 when the connector 160 is inserted therein.

In yet another aspect that is described below in more detail, the bag 410 includes a second flow control means 460 for venting stored gas under select conditions. For example, the first compartment 420 can include the second flow control means 460 for venting stored supplemental gas in situations where there is an excess amount of supplemental gas being stored in the first compartment 420. Since the first compartment 420 of the bag 410 has a limited volume, there is only a limited space for storing supplemental gas. If the volume of supplemental gas stored in the first compartment 420 exceeds the volume capacity of the first compartment 420, the bag 410 is at the risk of rupturing or there is a risk that the excess pressure in the first compartment 420 may damage the second flow control means 460.

It will be appreciated that the second compartment 430 is always in unobstructed fluid communication with the main body section 150. In other words, the gas (aerosolized medication) that is received through the first leg 120 flows into the main body section 150 and since there is no valve between the main body 110 and the second compartment 430, the aerosolized medication (gas) flows into the second compartment 430 where it is stored until the patient inhales at which time, the gas can flow to the patient interface member 200 as described below.

In accordance with the present invention, the system 100 includes patient interface member 200 in that the main body 110 can be integrally formed with the patient interface member 200 as described below or the main body 110 can be coupled to the patient interface member 200 using any number of techniques including but not limited to a mechanical fit, such as a frictional fit or other type of mechanical fit, such as a snap-fit attachment or by use of fasteners or the like. In the illustrated embodiment, the main body section 150 includes port 152 that is designed to mate with a complementary part of the patient interface member 200. The port 152 is in the form of a tubular structure that defines the top of the body 110. A frictional fit can be formed by inserting a male member into the port 152 resulting in the main body 110 and the patient interface member 200 being securely attached to one another.

In the illustrated embodiment, the patient interface member 200 is in the form of a face mask. The face mask 200 has a body section 210 that has a peripheral edge 212 that defines an edge of the face mask 200 that seats against the face of the wearer. In other words, when the face mask 200 is worn, the edge 212 is pressed against the face to form a seal therewith. The body section 210 has a front face or front surface 214 that represents the portion of the face mask 200 that is furthest away from the face of the wearer. The body section 210 has a convex shape since the nose of the patient must be received and accommodated within an interior 211 of the body section 210.

The face mask 200 has a fluid receiving section 220 that represents the portion of the face mask 200 that is coupled to the main body 110. The fluid receiving section 220 can thus be in the form of a hollow structure that extends outwardly from the body section 210 and is configured to interface with the patient interface port 152. For example, the fluid receiving section 220 can be frictionally received into the patient interface port 152 to form a mechanical fit therebetween. Other techniques can be used to couple the face mask 200 to the body section 110. The coupling between the face mask 200 and body section 110 is of a detachable type to permit the two components to be detached from one another, while still offering a sealed interface between the two.

The fluid receiving section 220 can extend outwardly from the body section 210 in any number of different manners. For example and as shown in FIG. 1, the fluid receiving section 220 extends downwardly from the body section 210. The fluid receiving section 220 actually represents the most forward section of the face mask 200.

The fluid receiving section 220 forms an interface with the body section 210 and an opening or entrance 230 is formed therebetween to define a flow channel or passage way between the fluid receiving section 220 and the body section 210. In the illustrated embodiment, the fluid receiving section 220 is slightly L-shaped in that it includes a longer leg 222 and a shorter leg 224 in which the opening 230 is formed. The relative lengths of the longer leg 222 and shorter leg 224 can be varied and are not critical.

In addition, the fluid receiving section 220 can have an L-shape where the longer leg is the leg that interfaces with the body section 210 and the shorter leg is the leg that is coupled to the main body 110. Other configurations for the fluid receiving section 220 are equally possible. For example, the fluid receiving section 220 can be a linear section and can be oriented so that it is substantially perpendicular to the body section 210.

In accordance with the present invention, the face mask 200 includes a third flow control means 500 that provides selective communication between the interior of the face mask 200 and the fluid receiving section 220, and thus, the attached main body 110. The third flow control means 500 is disposed in the opening 230. In one embodiment, the third flow control means 500 is a pivotable flap valve 502 that pivots on a pivot 512 that is part of a valve seat 510 and is disposed about the opening 230. The valve 502 thus pivots between a closed position where fluid is prevented from passing between the face mask 200 and the fluid receiving section 220 and an open position where fluid is permitted to flow between the fluid receiving section 220 and the face mask 200. The third flow control means 500 is a one-way valve in that the valve 502 can only open to permit fluid to flow in a direction from the main body 110 to the face mask 200.

In one embodiment, the valve 502 includes a pair of openings 503 formed therethrough and the pivot 512 is in the form of two pivot posts that extend outward from the valve seat 510. The valve 502 is coupled to the valve seat 510 by simply inserting the posts 512 into the openings 503 resulting in the valve 502 “hanging” from the posts 512. In other words, the valve 502 is carried by the posts 512 and in the closed position, the valve 502 completely occludes the opening 230 formed as part of the valve seat 510, thereby preventing fluid to flow into the face mask 200. When a force (e.g., fluid flow) is applied in a direction toward the interior of the face mask 200, the valve 502 pivots (swings) on the posts 512 to an open position. In the open position, fluid can flow from the fluid receiving section 220 through the opening 230 and into the interior of the face mask 200.

It will be appreciated that the shape and size of the valve 502 can vary so long as the opening 230 of the valve seat 510 has a complementary shape such that when the valve 502 closes, the opening 230 is completely occluded.

In accordance with the present invention, the third flow control means 500 has a safety feature 520 to prevent unwanted travel of the valve 502 in the unlikely event that the valve 502 becomes separated (detached) from the valve seat 510. More specifically, the safety feature 520 is in the form of an obstruction that prevents the valve 502 from moving into the interior of the face mask 200 after the valve 502 has become detached from the valve seat 510. Accordingly, the safety feature 520 prevents the valve 502 from traveling toward the patient’s mouth and possibly being inhaled by the patient as the patient inhales the aerosolized medication.

In the illustrated embodiment and as shown in FIG. 3, the safety feature 520 is in the form of a cage or mesh or screen structure that prevents the valve 502 from passing therethrough but does not adversely obstruct the flow of aerosolized medication into the interior of the facemask 200. In the illustrated embodiment, the safety feature 520 is in the form of a cage that has a frame structure 522 formed of a number of interconnected bars 524 with spaces 526 being defined between the bars 524. Each space 526 has dimensions that are less than dimensions of the valve 502 and therefore, the valve 502 cannot pass through any of the spaces 526.

In the illustrated embodiment, the safety feature 520 has a hemi-spherically shaped frame (dome shaped). For example, the frame 522 can have a circular base 530 that is attached to the valve frame 510 so that the valve opening 530 is in registration with the opening defined by the circular base 530. The frame 522 includes a first cross bar 532 that has a hemispherical shape and is attached to two points on the base 530 that are 180 degrees apart from one another. In addition, a second cross bar 534 is provided as part of the frame 522 and it has a hemi-spherical shape and is attached to two points on the base 530 that are 180 degrees apart from one another and preferably are 90 degrees apart from the two ends of the first cross bar 532. The frame 522 also includes an intermediate cross beam 536 that has a circular shape and disposed in a plane that is parallel to the plane containing the base 530. It will be appreciated that the above frame structure 522 is merely one exemplary frame structure and any number of other frame structures are equally possible so long as the valve 502 cannot pass through the frame structure 522.

When the frame 522 has the above structure, the valve seat 510 can be integrally attached to the base 530 and in particular, the posts 512 of the valve seat 510 can be integrally attached to the base 530, thereby permitting the valve 502 to hang within the base 530 of the frame structure 522.

As shown in FIG. 1, the frame 522 extends inwardly into the interior of the facemask 200 since the valve 502 opens inwardly into the interior of the facemask 200. The valve 502 opens inwardly since the gas flowing through the fluid receiving section 220 from the patient interface port 152 flows in this direction toward the interior of the facemask 200.

Conversely, when the patient exhales, the valve 502 closes and gas cannot flow from the interior of the facemask 200 into the fluid receiving section 220 and thus, the gas is prevented from flowing to body 100. Within the fluid receiving section 220, the valve 502 is generally positioned across from the mouth of the patient so that the aerosolized medication flowing through the valve 502 is effectively delivered to the patient's lungs.

In another embodiment, the valve 502 can be attached to the valve frame 510, the facemask 200, or other structure, such as the fluid receiving section 220, as a means of providing the safety feature. For example, a tether can be attached at one end of the valve 502 and at its other end, the tether is attached to a fixed structure, like the valve frame 510, facemask 200, etc. If the valve 502 ever becomes dislodged from the valve seat 510, the tether keeps the valve 502 attached to a structure and prevents the valve 502 from entering the patient's mouth during inhalation.

The body section 210 also includes a pair of flow control means that are in selective communication with the atmosphere to permit venting of the interior 211 of the body section 210. For example, fourth and fifth flow control means 240, 250 can be disposed in predetermined areas of the body section 210. In the illustrated embodiment, the flow control means 240, 250 are formed in cheek regions of the face mask 200.

The flow control means 240, 250 can be in the form of a pair of exhalation valve assemblies that have valves 244, 254, respectively, that seat against respective valve seats 246, 256. When the patient exhales, the exhaled gas exits the patient's mouth and flows into the interior 211 where it flows toward the flows control means 240, 250 since the valves 244, 254 are constructed to open when the patient exhales into the interior 211. Due to a pressure differential, the exhaled gas flows from the interior 211 toward and through the open valves 244, 254 and into the atmosphere.

In one embodiment, the flow control means 240, 250 are formed within a pair of protrusions 260, 270 (e.g., a boss) that extend outwardly from the body section 210. For example, the protrusions 260, 270 can be tubular protrusions that extend outwardly from the body section 210. The interiors of the protrusions 260, 270 are in fluid communication with the body section 210. The valves 244, 254 are disposed within the interiors of the protrusions 260, 270 along the lengths thereof.

The protrusions 260, 270 can also be used as a filter housing in that a filter element can be disposed in the protrusions 260, 270 or the filter element can be a separate part that is attached to the protrusion 260, 270. The filter element is designed to filter the exhaled gas from the patient before the exhaled gas is discharged into the atmosphere. In the embodiment where the filter element is a separate part, the physician can select the type of filter element that is to be used based on a number of different parameters. In addition, the size of the filter element can be selected based on a number of different parameters, including the size of the facemask 200 and size of the patient, etc.

The valves 244, 254 can have a construction that is the same as or similar to the above described valve structures that are supported and carried by pivot posts or the valves 244, 254 can have a different construction. For example, the valve can have a protrusion that is inserted into a central hub of a spoke shaped valve seat that has a number of spaces through which the gas flows when the valve lifts off the valve seat.

The second compartment 430 of the bag 410 is therefore intended to act as a main reservoir bag in that the second compartment 430 receives and holds the nebulized medication until the patient inhales. The second compartment 430 of the bag 410 thus expands until the patient inhales at which time the valve element 502 that is associated with face mask 200 opens and the inhalation of the patient draws the nebulized medication out of the second compartment 430 through the first leg 120, into the main body section 150 and then into the fluid receiving section 220 where it passes through the open valve 502 and into the interior of the face mask 200 where it is inhaled by the patient.

There are some circumstances where an insufficient amount of nebulized medication is present in the second compartment 430 of the bag 410. This may result because the flow rate of the nebulizer 400 is insufficient for the patient as when the patient has a greater body weight than the flow rate setting of the nebulizer 400. When this does occur, the patient experiences a very uncomfortable feeling in that the patient will experience an insufficient air flow to the lungs and therefore will begin to breathe more deeply and rapidly. In other words, the patient may begin feeling as though they need to gasp for air to breathe.

The present invention overcomes such potential deficiency in air flow to the patient by providing the first compartment 420 in the bag 410 which acts as a supplemental air source for the patient due to the second compartment 430 being attached to a supplemental gas source, generally indicated at 401. Preferably, the gas source 401 connects to the supplemental gas port 180 of the first fluid connector 160 as shown in the figures; however, it is possible for the gas source 401 to be directly connected to the first compartment 420 of the bag 410. In any event, the gas source 401 is directly and fluidly connected to the first compartment 420 and therefore, the gas is delivered into the first compartment 420. As with the flow of nebulized medication into the second compartment 430, the flow of the gas source 401 into the first compartment 420 causes the first compartment 420 to expand as the bag 410 is filled with gas.

It will be appreciated that the gas source 401 serves as a supplemental gas since gas stored in the first compartment 420 is in selective fluid communication with the main body section 150 and therefore, can flow to the patient under certain circumstances as discussed below. In other words, if there is insufficient gas in the form of nebulized gas in the second compartment 430, when the patient inhales, then the patient will not experience the above described breathing problems since the first compartment 420 can open to the patient through the main body section 150 and therefore, the patient can inhale the supplemental gas that is present in the first compartment 420 to make up for any shortfall in gas in the second compartment 430.

The gas source 401 typically has an associated valve assembly (not shown) that is external to the system 100 and is typically at the gas source 401 for controlling the flow rate of the gas source 401 into the first compartment 420. The valve assembly is preferably an adjustable valve that controls the flow rate of the supplemental gas into the first compartment 420. Any number of different valve mechanisms are suitable for this type of application and typically include an adjustable part, such as a dial, that permits the physician to easily alter and change the flow characteristics. For example, the valve mechanism can include an adjustable member that when manipulated either sequentially closes or opens the opening formed in the conduit that delivers the supplemental gas to the first compartment 420.

Thus, the physician can initially set the valve at one setting which the physician believes will provide a sufficient supplemental gas flow into the first compartment 420 based on the physician's past experiences and based on certain characteristics of the patient, such as the size and weight of the patient. For example, when the patient is a large adult or even a large child, the flow rate of the nebulized medication into the second compartment 430, even when it is set at a maximum flow rate, may not be sufficient and therefore, this could result in the patient receiving a low level of air and feeling the above noted discomfort. The gas source 401 thus supplements the gas flow of the nebulizer 400 and makes up for any deficiency so that the patient breaths smoothly throughout the procedure.

When setting the valve, the physician will keep in mind that it may not be desirable to set the flow rate of the supplemental gas at too high a value since this will result in the first bag compartment 420 expanding and also, results in the supplemental gas source 401 mixing with the nebulized medication as the patient inhales, thereby causing a decrease in the inhaled concentration of the medication. As mentioned before, it is desirable to try to keep as fixed as possible the concentration of the inhaled medication.

As previously mentioned, the first compartment 420 includes the second flow control means 460 for venting the first compartment 420 when an excess buildup of supplemental gas occurs in the first compartment 420 due to insufficient flow of the supplemental gas into the main body section 150. Thus, the second flow control means 460 opens when the first compartment 420 expands to a maximum amount prior to rupture of the first compartment 420.

In the event that the initial setting of the valve is not optimal in that the too much supplemental gas is being delivered to the first bag compartment 420 or too little supplemental gas is being delivered to the first bag compartment 420, the physician simply needs to make the necessary adjustment to the valve to either immediately reduce or increase, respectively, the supplemental gas flow into the first compartment 420. This can be done by simply turning or otherwise manipulating the valve. It is also very easy for the physician to determine whether the flow rate of the supplemental gas source 401 is optimal since the physician can observe the bag 410 and more particularly, can observe whether either the first compartment 420, the second compartment 430 or both compartments 420, 430 appear to be excessively collapsed (thus indicating an increase in flow rate is needed) or excessively expanded or extended (thus indicating a decrease in flow rate is needed). The physician can simply and immediately alter the flow rate and thus, the system 100 is tailored to be used with a whole range of different types of patients, from small infants up to large adults.

It will also be appreciated that as described above, a flow metering feature can be associated with the delivery of the supplemental gas to the first compartment 420.

It will be appreciated that the combination accessory 100 and face mask 200 of the present invention has a number of specifically defined gas flow paths that each has its own level of flow resistance which causes the flow paths to have a preferential flow order in terms of which flow paths the gas will flow to first and second, etc., when the patient inhales. The gas will first flow according to a first flow path (primary flow path) generally indicated by arrow 600. The first flow path 600 includes flow of the aerosolized medication (primary gas) from the nebulizer, MDI, or the like 400 and in particular, the first flow path 600 has two components, namely, a first component where the aerosolized medication flows through the first leg 120 and directly into the main body section 150 and then into the fluid receiving section 220 of the face mask 200 and when the valve 502 opens, the aerosolized medication enters the interior of the face mask 200 where it is inhaled by the patient. The second component of the primary flow path is defined initially by flow of the aerosolized medication into the second compartment 430 of the bag 410 from the main body section 150 and then upon inhalation by the patient, the aerosolized medication that is stored in the second compartment 430 then flows back into the main body section 150 and then the fluid receiving section 220 of the face mask 200 and when valve 502 opens, the gas flows to the patient.

It will be appreciated that the first flow path 600 only has a single flow control means, namely, the valve 502, that opens when the patient inhales. Thus, the only resistance that is encountered along this flow path is due to the valve 502. Since the first flow path 600 is the flow path of least resistance, the gas prefers to flow along this flow path 600.

A second flow path 610 is defined, in part, by the first compartment 420 and relates to the flow of supplemental gas. In particular and as described above, the supplemental gas flows from its source through the supplemental gas port 180 and into the first compartment 420 when the first flow control means 300 (valve 302) is closed, the supplemental gas flows into the first compartment 420. When the first compartment 420 is open, the gas flowing through the supplemental gas port 180 flows into the main body section 150 where the supplemental gas flows into the fluid receiving section 220 and then into the interior of the face mask 200 when the valve 502 opens upon inhalation by the patient. It will therefore be appreciated that in order for the supplemental gas to reach the patient, the supplemental gas must pass through two flow control means, namely, the valves 302, 502. The second flow path 610 thus includes one additional valve compared to the first flow path 600 and thus has increased flow resistance compared to the first flow path 600 and as a result, the primary gas flow (aerosolized medication) represents the preferred gas flow path due to their only being a single flow control means along its pathway 600 as opposed to the two flow control means along the second flow path 610.

It will also be appreciated that the system 100 also includes a third gas flow path 620 that represents the inflow of atmospheric air as a backup to the aerosolized medication and the supplemental gas when both of these gas supplies are insufficient for a particular patient's breathing. As previously described, in the event that during inhalation by the patient, there is an insufficient amount of gas to breathe, the inhalation safety valve 310 will open to the atmosphere, thereby permitting air from the outside to flow into the first connector 160 and the second leg 130 where it flows into the main body section 150 and then ultimately through the fluid receiving section 220 and into the interior of the face mask 200. The atmospheric air thus has to pass through three different flow control means prior to entering the interior of the face mask 200 where it is inhaled by the patient. The third gas flow path 620 can be thought of as a tertiary flow path since atmospheric gas entering the face mask 200 has to pass through three separate flow control means before being delivered to the patient. As a result, there is an increased level of resistance along this flow path compared to the other flow paths 600, 610.

It will also be appreciated that the inhalation safety valve 310 can be constructed so that more force is required to open this particular valve compared to the other valves, such as the valve 302 and valve 502. As a result, only when the patient is deeply inhaling, as is the case when there is insufficient primary air and supplemental gas, does the inhalation safety valve 310 open to permit atmospheric air to be delivered to the patient.

The degree of resistance along the tertiary flow path 620 is greater than the other two flow paths 600, 610.

One will appreciate that the accessory 100 and face mask 200 are constructed so that there is maximum medication flow due to the creation of the different flow paths. By structuring the primary flow path to include the flow of the aerosolized medication, the system of the present invention is designed so that the aerosolized medication flows to the face mask 200 as opposed to flowing directly into the second compartment 430 and since valve 302 is between the location where the supplemental gas flows in and the main body section 150, the supplemental gas is a secondary gas compared to the aerosolized medication flowing through the first leg 120.

In particular, the first leg 120 through which the aerosolized medication is received does not include a valve and therefore, the aerosolized medication can flow directly into the fluid receiving section 220 of the face mask 200 without encountering a valve member. The primary flow path is thus the flow path along which the aerosolized medication flows, the secondary flow path is the flow path along which the supplemental gas flows, and the tertiary flow path is the flow path along which atmospheric air flows as a safety gas flow.

The flow resistances along the various flow paths and placement of valves are carefully selected so that when the patient demand is less than stored aerosolized medication in the second compartment 430, there is no flow from the first compartment 420 that stores the supplemental gas and if the demand is greater than a threshold, communication is provided between the first compartment 420 and the face mask 200 for delivery of supplemental gas to the patient.

It will also be appreciated that the system of the present invention is constructed so that the there is a medicated storage reservoir (second compartment 430) and a non-medicated storage reservoir (first compartment 420). Further, a single gas supply can be used to deliver gas to the nebulizer 400 as well as delivering as to the supplemental gas port 180 where the gas flows into the first compartment 420 and is available to supplement the aerosolized medication. This is an improvement over using two separate gas sources, one for the aerosolized medication and one for the supplemental gas.

The above described system and variations thereof can be used in conventional inhalation equipment settings and thus can be used with conventional nebulizers to overcome the deficiencies that are associated with the prior art aerosol inhalation systems. In addition, the use of a supplemental gas source ensures that the accessory and the disclosed aerosol inhalation system is suitable for use with all types of patients from small infants to large adults irregardless of whether the flow rate of the nebulizer by itself is sufficient to support a normal breathing pattern of the patient.

It will also be appreciated that the first leg 120 can be capped or otherwise sealed as when nebulizer 400 is not used with the respective system. In this design, the bag 410 can serve as a means for delivering a gas, such as oxygen or heliox, etc., to the patient. In particular, a gas source provides gas which is routed through the second compartment 430 of the bag 410 and into the main body section 150.

Figure 4:
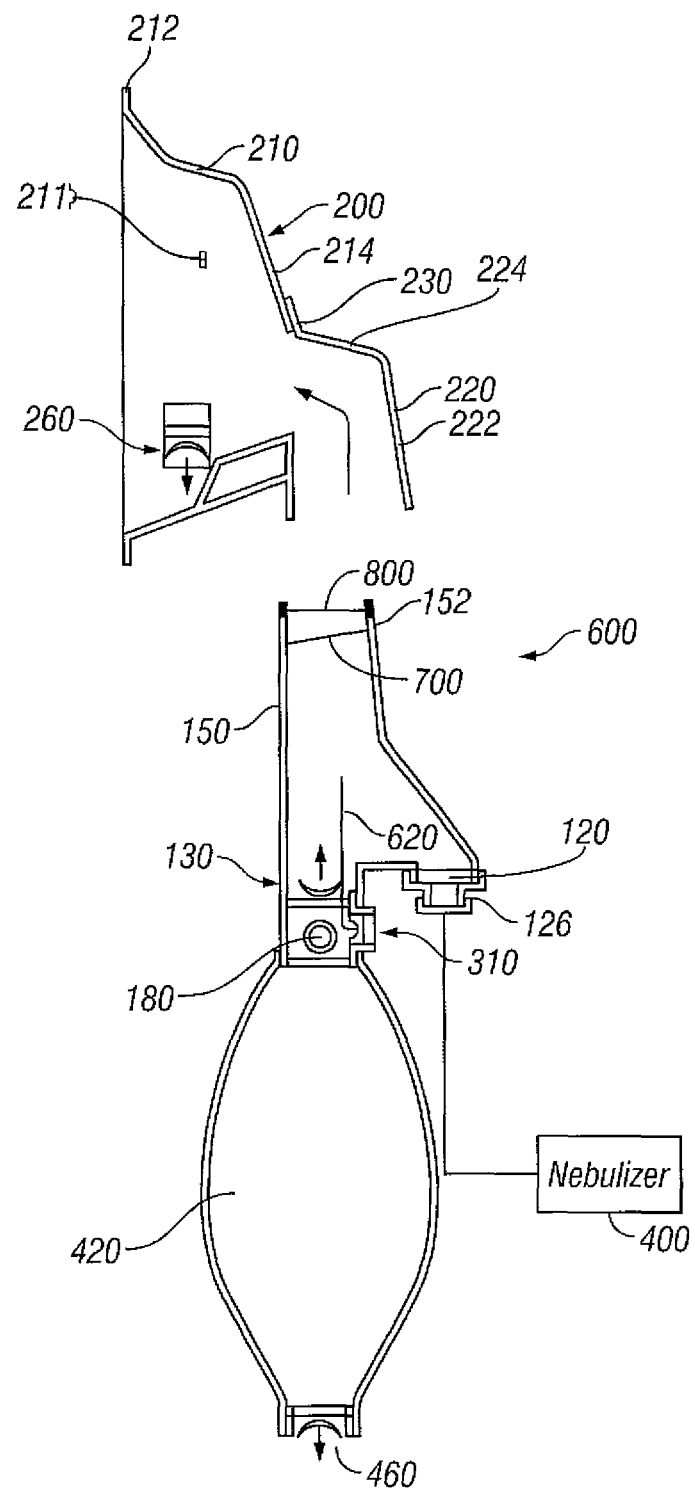
FIG. 4 is an exploded cross-sectional view of a patient interface member according to another embodiment.
Figure 5:
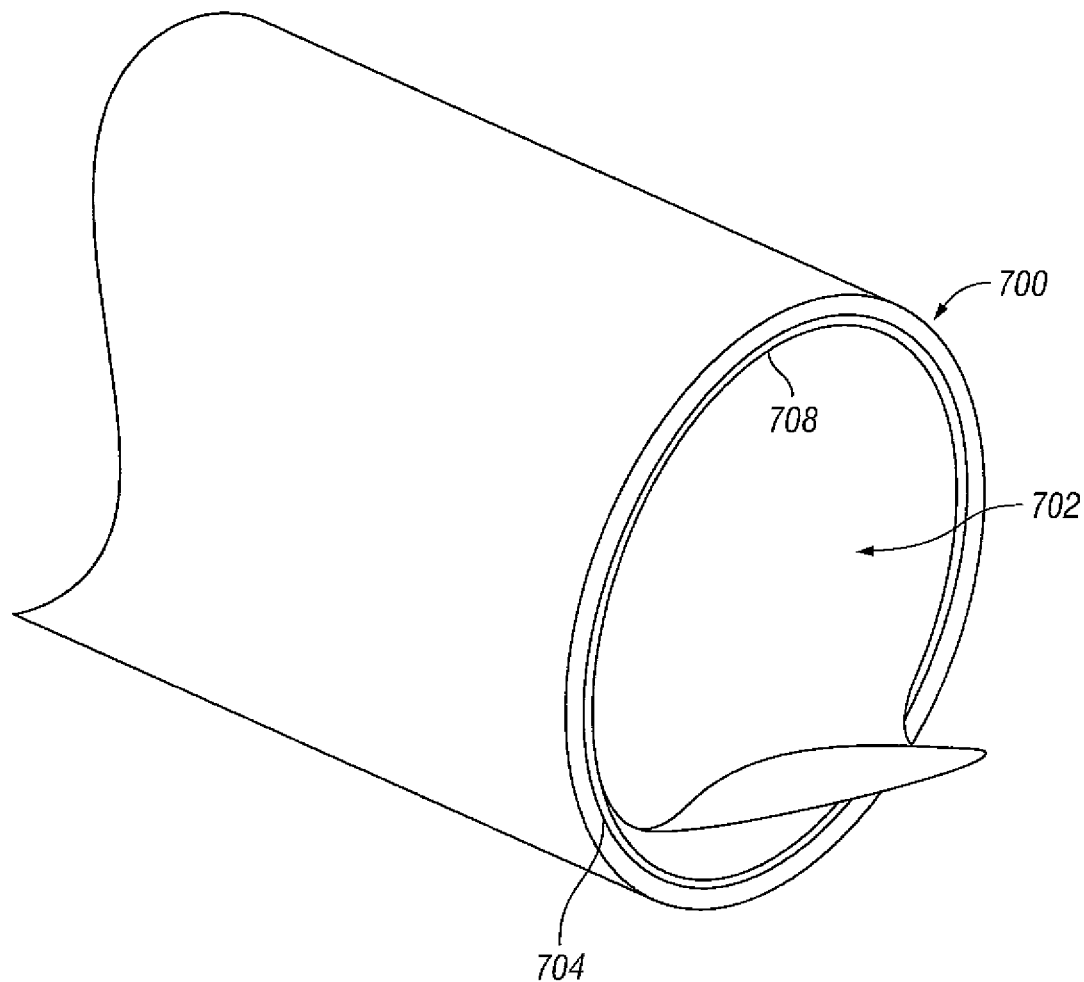
FIG. 5 is a close-up perspective of an inhalation valve that is part of the system of FIG. 4.

Now turning to FIGS. 4-5 in which another embodiment of the present invention is illustrated. This embodiment is similar to the first embodiment in that it shares some common components as described below.

The main difference between system 600 and the previous system 100 is the interface between the main body 110 and the face mask 200. The components that are in common to both designs are shown and numbered alike.

In system 600, the main body section 150 is also in the form of a leg that terminates in the patient interface port 152 that is configured to mate with the patient interface member 200. In contrast to the system 100, the main body section 150 of the system 600 also includes a third flow control means 700 that is in the form of a valve. However, in contrast to the valve design of the third flow control means 500 of the system 100, the third flow control means 700 is in the form of a non-pivotal valve. More specifically, the main body section 150 can be in the form of a tubular leg structure (e.g., circular shaped tube) and the third flow control means 700 is disposed within the main body section 150 proximate the distal end of the main body section 150.

The third flow control means 700 includes a valve member 702 that attaches to a valve seat 704 or attaches directly to an inner wall of the main body section. The valve member 702 is a flexible structure that is capable of rolling on itself. For example, the valve member 702 is formed of a polymeric material that can freely bend and flex as a force is applied thereto. The valve member 702 is not pivotally attached to the main body section 150 but instead is fixedly attached thereto. For example, one or more points or locations (generally indicated at 708) of the valve member 702 can be attached to the inner surface of the main body section 150 using conventional means, including bonding or welding (heat weld) the valve member 702 to the main body section 150. As is known, a pivot is a point or short shaft on the end of which something rests and turns, or upon and about which something rotates or oscillates and therefore since the valve member 702 is fixedly attached to the main body section 150, the valve member 702 is not pivotally attached to the main body section 150 since it can not turn, rotate or oscillate about the point of attachment between the valve member 702 and the main body section 150.

Instead, the valve member 702 will fold along its body as a result of a force being applied to the valve member 702. This flexing and bending of the valve member 702 along the body of the valve member creates a space through which a fluid (e.g. air) can travel (toward and to the patient in the case of the valve member 702 being an inhalation valve). The bending of the valve member 702 does not occur at the point of attachment to the main body section 150 but instead it occurs along the free body portions of the valve member 702. It will be appreciated that the location(s) where the valve member 702 flexes, folds and bends will vary depending upon a number of different parameters. For example, the degree of force against the body of the valve member 702 will cause the flex point or roll location to vary. When no force is applied, the valve member 702 sealingly closes the main body section 150 by being in sealed contact with the inner wall thereof. FIG. 5 shows the valve member 702 being partially open as by a folding of the valve member 702 so as to create an opening to permit fluid to pass through the main body section 150 into the face mask 200.

The main body section 150 is mated to and securely attached to the patient interface member 200 (face mask) using conventional techniques. For example, a mechanical fit (interface fit) can be provided between the face mask 200 and the main body section 150 by simply inserting one of these components into the other component. In the illustrated embodiment, the fluid receiving section 220 is dimensioned so that the main body section 150 can be inserted therein so as to establish a frictional fit therebetween. This fit and attachment between the two components is of a removable or detachable type to permit the two components to be easily separated from one another. Other methods of attaching the two together can be used.

In order to ensure that the valve member 702 remains attached to the main body section 150, a safety feature 800 can optionally be provided. For example, the safety feature 800 can be in the form of a screen or some type of barrier that is disposed across the main body section 150. The screen 800 does not unnecessarily block the flow of the aerosolized medication but does prevent passage of the valve member 702 through the main body section 150 to the interface member 200 (face mask). This protects against the unlikely event that the valve member 702 becomes dislodged and separated from the main body section 150. The screen 800 can be disposed across the opening of the main body section 150 and attached to an inner wall thereof near or at the free distal end of the main body section 150. It will also be appreciated that the safety member 800 can be placed in another location, such as within the fluid receiving section 220 since the safety member 800 only has to be located downstream of the valve member 702 and prior to the inner compartment of the face mask 200.

Having described embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A device for use in an aerosol inhalation system for delivering aerosolized medication comprising:
    a means for generating aerosolized medication;
    a reservoir having a first compartment and a second compartment;
    an accessory having a housing that is operatively connected to the means for generating aerosolized medication such that the aerosolized medication is delivered to the housing, wherein the housing includes a first leg that is fluidly attached to the means of generating aerosolized medication, a second leg that is in selective communication with the first storage compartment and a third leg that is always in fluid communication with the second storage compartment, wherein there is an unobstructed flow path between the first and third legs; and
    a patient interface member removably connected to the housing and being separate therefrom, the patient interface member for placement about a face of the patient and in communication with a mouth of the patient for delivering the aerosolized medication, wherein the patient interface member comprises a face mask that includes a main body and an integral fluid receiving section that extends therefrom and is sealingly coupled to a patient interface section of the housing to permit the aerosolized medication to selectively flow into the interior of the face mask by passing through the fluid receiving section, wherein there is an unobstructed flow path between the second storage compartment and the fluid receiving section of the face mask, the face mask having a first flow control means that is free of attachment to the housing and is integral to the face mark and is positionable between an open position where aerosolized medication flows into an interior of the mask when the patient interface section of the housing is mated with the fluid receiving section of the face mask and when the patient inhales and a closed position when the patient exhales, the first flow control means being positioned within a flow path that is defined by the fluid receiving section, the exhaled gas being vented from the interior of the patient interface member through at least one vent port that is part of the face mask;
    wherein the housing includes a main body section that is in communication with first end of each of the first, second and third legs, the main body section having a patient interface section that sealingly mates with a complementary fluid receiving section of the patient interface member so that gas flowing into and through the housing is directed to the patient interface member;
    wherein the second compartment is for storing aerosolized medication that is delivered into the housing through the first leg and flows through the third leg to the second compartment and the first compartment stores non-medicated gas;
    wherein the second leg has a second flow control means associated therewith and a supplemental gas port associated therein for receiving a supplemental gas, the second flow control means being in the form of an inhalation valve that is disposed between the main body section and the supplemental gas port such that a clear open flow path is always defined between the supplemental gas port and the first compartment such that the supplemental gas can flow into the main body section only when the second flow control means is open; and when the second flow control means is closed, the supplemental gas flows into the first compartment where it is stored until the second flow control means opens.

2. The device of claim 1, wherein the first flow control means comprising a first inhalation valve that is attached to a valve seat that is disposed between an interface between the main body of the face mask and one end of the fluid receiving section.

3. The device of claim 2, further comprising a valve safety feature to prevent the first inhalation valve from entering the patient's mouth in the event that the first inhalation valve becomes separated from the face mask, the valve safety feature being disposed between the first inhalation valve and the interior of the face mask.

4. The device of claim 3, wherein the valve safety feature comprises a cage structure that surrounds the first inhalation valve and is attached to the face mask and permits the first inhalation valve to fully open, the cage structure being formed of interconnected bars that define a plurality of interstitial spaces.

5. The device of claim 4, wherein the cage has a hemispherical shape.

6. The device of claim 1, further comprising at least one exhalation valve assembly that is part of the patient interface member, the exhalation valve being provided in a protrusion that extends outwardly from the patient interface member.

7. The device of claim 6, wherein the protrusion is configured to mate with a filter attachment for filtering the exhaled gas.

8. A device for use in an aerosol inhalation system for delivering aerosolized medication comprising:
a means for generating aerosolized medication;
a reservoir having a first compartment and a second compartment;
an accessory having a housing that is operatively connected to the means for generating aerosolized medication such that the aerosolized medication is delivered to the housing, wherein the housing includes a first leg that is fluidly attached to the means of generating aerosolized medication, a second leg that is in selective communication with the first storage compartment and a third leg that is always in fluid communication with the second storage compartment, wherein there is an unobstructed flow path between the first and third legs and there is an unobstructed flow path between the second storage compartment and the fluid receiving section of the face mask; and
a patient interface member removably connected to the housing and being separate therefrom, the patient interface member for placement about a face of the patient and in communication with a mouth of the patient for delivering the aerosolized medication, wherein the patient interface member comprises a face mask that includes a main body and an integral fluid receiving section that extends therefrom and is sealingly coupled to a patient interface section of the housing to permit the aerosolized medication to selectively flow into the interior of the face mask by passing through the fluid receiving section, the face mask having a first flow control means that is free of attachment to the housing and is integral to the face mark and is positionable between an open position where aerosolized medication flows into an interior of the mask when the patient interface section of the housing is mated with the fluid receiving section of the face mask and when the patient inhales and a closed position when the patient exhales, the first flow control means being positioned within a flow path that is defined by the fluid receiving section, the exhaled gas being vented from the interior of the patient interface member through at least one vent port that is part of the face mask;
wherein the housing includes a main body section that is in communication with first ends of each of the first, second and third legs, the main body section having a patient interface section that sealingly mates with a complementary fluid receiving section of the patient interface member so that gas flowing into and through the housing is directed to the patient interface member;
wherein the second compartment is for storing aerosolized medication that is delivered into the housing through the first leg and flows through the third leg to the second compartment and the first compartment stores non-medicated gas;
wherein the second leg has a second flow control means associated therewith and a supplemental gas port associated therein for receiving a supplemental gas, the second flow control means being disposed between the main body section and the supplemental gas port so that the supplemental gas can flow into the main body section only when the second flow control means is open; and when the second flow control means is closed, the supplemental gas flows into the first compartment where it is stored until the second flow control means opens;
wherein the second leg has a safety flow control means that is associated therein and is open to atmosphere and opens only when there is insufficient gas flow of both aerosolized medication and supplemental gas.

9. A device for use in an aerosol inhalation system for delivering aerosolized medication comprising:
a means for generating aerosolized medication from a single source of gas;
a housing that is operatively connected to the means for generating aerosolized medication such that the aerosolized medication is delivered to a main port of the housing, the housing having a supplemental gas port for receiving a flow of supplemental gas;
a patient interface member in the form of a face mask that is fluidly coupled to the housing and for placement about a face of the patient and in communication with a mouth of the patient for delivering the aerosolized medication, the face mask having a first inhalation valve that is part of the face mask and is positionable between an open position where aerosolized medication flows into an interior of the patient interface member when the patient inhales and a closed position when the patient exhales, the exhaled gas being vented from the interior of the face mask through at least one vent port that is part of the face mask;
a flexible, expandable reservoir having a first compartment that is in fluid communication with the supplemental gas port for receiving and storing the supplemental gas and a second compartment that is always in fluid communication with the main port for receiving and storing the aerosolized medication when the first inhalation valve is in the closed position, the second compartment being fluidly attached to the housing at a location remote from but in fluid communication with the main port, wherein the reservoir comprises a bifurcated bag and the first compartment has a different volume compared to the second compartment, the reservoir being removably attached to the housing; and
a safety vent formed as part of the first compartment and open to atmosphere, the safety vent opening to vent the supplemental gas in the first compartment to atmosphere when an excess of supplemental gas is stored in the first compartment, the safety vent comprising a valve that is formed in expandable material that forms the first compartment of the reservoir.

10. The device of claim 9, wherein the vent port is provided in a protrusion that extends outwardly from the face mask and when it opens, gas within the interior of the face mask is vented to atmosphere.

11. The device of claim 9, wherein the housing includes first, second and third legs, the first leg including the main port and being in fluid communication with the means for generating aerosolized medication, the second leg being in fluid communication with the supplemental gas and the third leg being in fluid communication with the second compartment of the reservoir that is fluidly separated from the first compartment, the second leg being in fluid communication with a second flow control means in the form of a second inhalation valve that is located such that gas flowing through the supplemental gas port and gas stored in the first compartment of the reservoir must flow through the second inhalation valve to flow to the patient interface member and be inhaled by the patient after passing through the first inhalation valve.

12. The device of claim 11, wherein the housing is configured as a tripod structure and includes a first hollow fitting that mates with a second hollow fitting that is part of the patient interface member in a sealed manner to permit gas to flow from the housing into the patient interface member and then to the patient.

13. A device for use in an aerosol inhalation system for delivering aerosolized medication comprising:
  a means for generating aerosolized medication from a single source of gas;
  a housing that is operatively connected to the means for generating aerosolized medication such that the aerosolized medication is delivered to a main port of the housing, the housing having a supplemental gas port for receiving a flow of supplemental gas;
  a patient interface member in the form of a face mask that is fluidly coupled to the housing and for placement about a face of the patient and in communication with a mouth of the patient for delivering the aerosolized medication, the face mask having a first inhalation valve that is part of the face mask and is attached to and movable relative to a valve seat structure and is positionable between an open position where aerosolized medication flows into an interior of the patient interface member when the patient inhales and a closed position when the patient exhales, the exhaled gas being vented from the interior of the face mask through at least one vent port that is part of the face mask; and
  a valve safety feature to prevent the first inhalation valve from entering the patient's mouth in the event that the first inhalation valve becomes separated from the face mask, the valve safety feature disposed between the first inhalation valve and the patient's mouth, the valve safety defining a structure that allows air to flow therethrough regardless of a position of the first inhalation valve, wherein the valve safety feature has a frame with an opening being defined therein, the valve seat structure being integrally attached to the frame of the valve safety feature so as to allow the valve to move within a hollow interior space defined within the frame of the valve safety structure.

* * * * *